US009354155B2

(12) United States Patent
Chu et al.

(10) Patent No.: US 9,354,155 B2
(45) Date of Patent: May 31, 2016

(54) CELL COUNTING SYSTEMS AND METHODS (75) Inventors: Daniel Chu, Hercules, CA (US); Eli A. Hefner, Fairfield, CA (US); Yann Jouvenot, Benecia, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 747 days.

(21) Appl. No.: 13/483,771

(22) Filed: May 30, 2012

(65) Prior Publication Data
US 2012/0314092 A1 Dec. 13, 2012

Related U.S. Application Data (60) Provisional application No. 61/491,703, filed on May 31, 2011.

(51) Int. Cl.
G01N 15/14 (2006.01)
G01N 15/10 (2006.01)

(52) U.S. Cl.
CPC .... G01N 15/1463 (2013.01); *G01N 2015/1006* (2013.01)

(58) Field of Classification Search
CPC ............................. G02B 21/367; G01N 17/00
USPC ............................................ 348/79; 382/128
See application file for complete search history.

(56) References Cited

U.S. PATENT DOCUMENTS

| 4,171,866 | A | 10/1979 | Tolles | |
|---|---|---|---|---|
| 2004/0136581 | A1* | 7/2004 | Ellis | G01N 15/1475 382/128 |
| 2004/0241769 | A1 | 12/2004 | Crews et al. | |
| 2006/0187442 | A1* | 8/2006 | Chang | G01N 15/147 356/39 |
| 2008/0032325 | A1* | 2/2008 | DiMarzio et al. | 435/29 |
| 2008/0212172 | A1* | 9/2008 | Zhu | G01N 21/6458 359/383 |
| 2010/0328766 | A1 | 12/2010 | Griffin et al. | |
| 2011/0176051 | A1* | 7/2011 | Randers-Pehrson et al. | 348/349 |
| 2011/0211058 | A1 | 9/2011 | McCollum et al. | |
| 2011/0261164 | A1* | 10/2011 | Olesen | G01N 15/1475 348/46 |
| 2012/0013727 | A1 | 1/2012 | Breniman et al. | |
| 2012/0015392 | A1 | 1/2012 | Guo | |
| 2012/0218379 | A1* | 8/2012 | Ozcan et al. | 348/40 |
| 2012/0295300 | A1 | 11/2012 | Heng et al. | |

OTHER PUBLICATIONS

International Search Report and Written Opinion of PCT/US2012/040251 mailed Aug. 21, 2012, 17 pages.
General Electronics Healthcare Application note 28-9673-96 AA in Cell Analyzer 2000, Dec. 1, 2009, pp. 1, 3.
Extended European Search Report of EP Patent Application No. 12792944, dated Oct. 10, 2014, 25 pages total.

* cited by examiner

*Primary Examiner* — William C Vaughn, Jr.
*Assistant Examiner* — Jerry Jean Baptiste
(74) *Attorney, Agent, or Firm* — Kilpatrick Townsend and Stockton LLP (57) ABSTRACT

An automated system captures multiple digital images of a sample, from different viewing areas of the sample. The images are analyzed and a test result may be reported based on the count of cells in all of the digital images. The system may be especially applicable to the testing of samples having low cell concentrations, as the variability between tests may be reduced as compared with a system that bases its test results on only a single image of the sample. The system may count the cells in a first digital image of the sample, and may capture or analyze one or more additional digital images only when it is recognized that additional measurements are needed to ensure adequate accuracy and repeatability of the test.

26 Claims, 10 Drawing Sheets

CELL COUNTING SYSTEMS AND METHODS

CROSS-REFERENCES TO RELATED APPLICATIONS

This application claims priority to U.S. Provisional Patent Application No. 61/491,703, filed May 31, 2011 and titled "Cell Counting Systems and Methods", the entire disclosure of which is hereby incorporated by reference herein for all purposes.

BACKGROUND OF THE INVENTION

Cytometry is a technical specialty concerned with the counting and characterization of biological cells. For example, the concentrations and relative numbers of red and white cells in a sample of a patient's blood may be of interest in assessing the patient's overall health, in diagnosing disease, or for other uses.

Automated cell counting devices have become common. For example, a blood sample may be placed into a sample holder, and a camera or other device having camera-like capabilities may take a digital photograph of the sample. An automated system may then analyze the digital photograph to identify and count the cells present and report the results.

It is generally desirable to improve the accuracy and repeatability of cell counts.

BRIEF SUMMARY OF THE INVENTION

According to one aspect, a system includes a sensing system that produces a digital image of a viewing area of a sample holder, the sample holder holding a set of cells, and a motion system that changes the relative positions of the sample holder and the sensing system to a plurality of configurations, such that the viewing area encompasses a different viewable portion of the sample holder in each configuration. The encompassed viewable portions are arranged generally transversely with respect to a primary loading direction of the sample into the sample holder. The system also includes a controller that directs the sensing system to capture a digital image when the sample holder and sensing system are in each of the plurality of configurations. In some embodiments, the system further includes a computerized analyzer that analyzes the digital images and counts the cells detected in all of the digital images. The controller may perform the function of the computerized analyzer. The system may further include a light source that illuminates the viewing area. In some embodiments, the viewable portions of the sample holder encompassed by the viewing area in the plurality of configurations do not overlap. The motion system may further include a translation mechanism that moves the sample holder in translation. The motion system may further include a rotation mechanism that moves the sample holder in rotation. In some embodiments, the system further includes an enclosure housing at least some of the system and defining a slot into which the sample holder is inserted, and the motion system rotates the sample holder in a rocking motion while one end of the sample holder remains between sides of the slot. The rotation system may rotate the sample holder about a point at the slot. The motion system may include a motor that moves the sample holder under control of the controller. In some embodiments, the plurality of configurations includes at least three configurations. In some embodiments, the system further includes the sample holder, and the viewable portions of the sample holder are located in a single window of the sample holder. In some embodiments, the system further includes the sample holder, and the viewable portions of the sample holder are located in different windows of the sample holder. At least two windows may hold different sample materials.

According to another aspect, a method includes capturing, using a sensing system, a first digital image of a first viewable portion of a sample containing cells, and reconfiguring the sensing system and sample such that the sensing system images a second viewable portion of the sample. The first and second viewable portions are arranged generally transversely with respect to a primary loading direction of the sample into a sample holder holding the sample. The method further includes capturing a second digital image of the second viewable portion. In some embodiments, the method further includes analyzing, using a computerized analyzer, the first and second digital images and counting the cells detected in the digital images, and reporting a test result based on the count of the cells in both the first and second images. In some embodiments, the method further includes reconfiguring the sensing system and sample such that the sensing system images a third viewable portion of the sample, capturing a third digital image of the viewing area, and analyzing the third digital image and counting the cells detected in the third digital image, wherein reporting a test result based on the count of the cells in both the first and second images comprises reporting a test result based on the count of cells in all three of the digital images. In some embodiments, the first viewable portion and the second viewable portion do not overlap. Reconfiguring the sensing system and sample may include moving the sample. Moving the sample may include moving the sample in translation, in rotation, or in a combination of translation and rotation. Reconfiguring the sensing system and sample may include moving at least a portion of the sensing system. In some embodiments, reconfiguring the sensing system and sample includes moving both the sample and at least a portion of the sensing system. The first and second viewable portions may be located in a single window of the sample holder. In some embodiments, the first and second viewable portions are located in different windows of the sample holder.

According to another aspect, a method of counting cells includes capturing, using a sensing system, a first digital image of a first viewable portion of a sample containing cells. The first digital image is analyzed, using a computerized analyzer, to obtain a first count of the cells present in the first digital image. The method further includes comparing the count with a threshold count. When the count is below the threshold count, the sensing system and sample are reconfigured such that the sensing system images a second viewable portion of the sample, a second digital image is captured of the second viewable portion, and the second digital image is analyzed and a test result is reported based on the count of the cells present in the first and second digital images. When the count is above the threshold count, a test result is reported based on a count of the cells present in the first digital image without capturing a second digital image. In some embodiments, the first and second viewable portions are arranged generally transversely with respect to a primary loading direction of the sample into a sample holder. In some embodiments, the first and second viewable portions are arranged generally parallel with respect to a primary loading direction of the sample into a sample holder. In some embodiments, the count is a first count and the threshold count is a first threshold count, and the method further includes, when the first count is below the first threshold count; analyzing the first and second digital images to compute a second count of the cells present in the first and second digital images; comparing the second count with a second threshold count; when the second count is below the second threshold count, reconfiguring the sensing system and sample such that the sensing system images a third viewable portion of the sample; capturing a third digital image of the third viewable portion; and analyzing the third digital image and reporting a test result based on a count of the cells present in the first, second, and third digital images; and when the second count is above the second threshold count, reporting a test result base on a count of the cells present in the first and second digital images without capturing a third digital image. The first and second concentration thresholds may be the same.

According to another aspect, a method of counting cells includes capturing, using a sensing system, a plurality of digital images of different viewable portions of a sample containing cells. A first one of the plurality of digital images is analyzed, using a computerized analyzer, to obtain a first count of the cells present in the first digital image, and the count is compared with a threshold count. When the count is below the threshold count, at least one additional image from the plurality of digital images is analyzed, and a test result is reported based on the count of the cells present in the analyzed digital images. When the count is above the threshold count, a test result is reported based on a count of the cells present in the first digital image without analyzing any further digital images.

According to another aspect, a sample holder includes a body configured for insertion into a cell counting system, and a plurality of windows in the body for receiving samples of one or more materials containing cells to be counted. The windows are arranged transversely or parallel with respect to a primary loading direction of the sample holder into the cell counting system. The windows may be spaced apart from each other by a distance corresponding to the spacing of multiple viewing areas of the cell counting system.

DETAILED DESCRIPTION OF THE INVENTION

Figure 1:
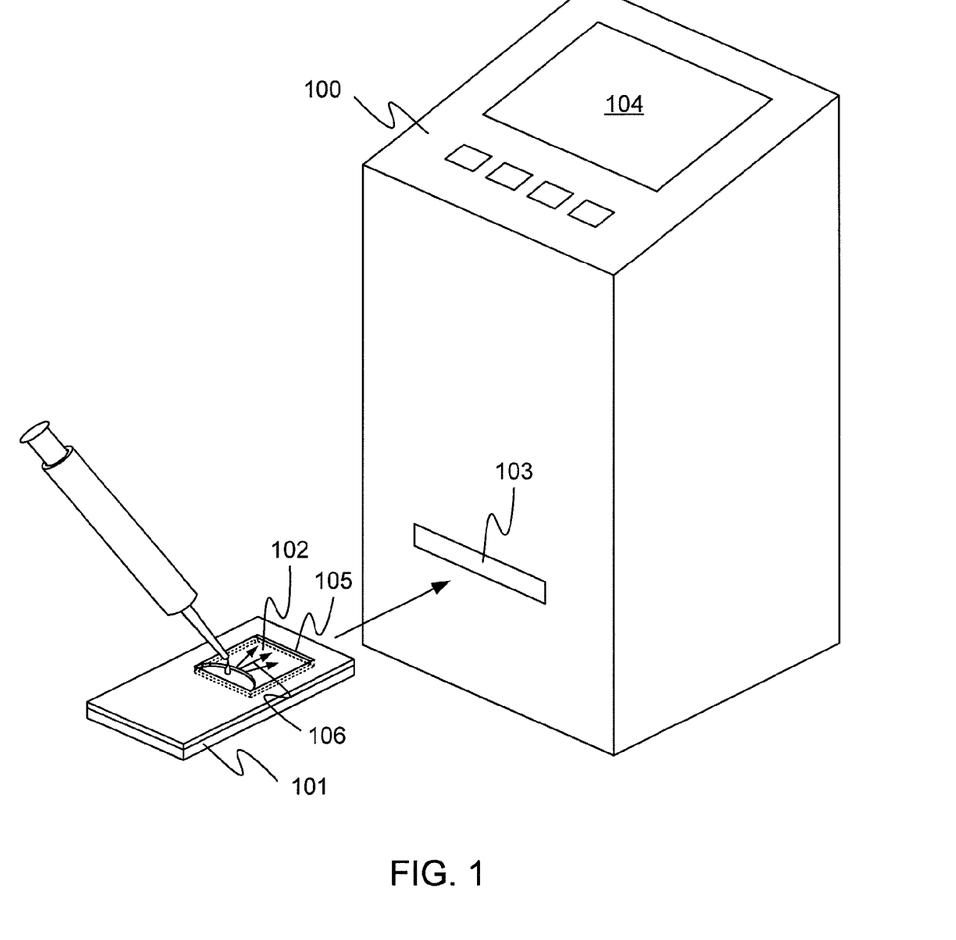
FIG. 1 illustrates a cell counting system, in accordance with an embodiment of the invention.

FIG. 1 illustrates a cell counting system 100, in accordance with an embodiment of the invention. To use cell counting system 100, a user may place a sample containing cells to be counted, for example a blood sample or other sample, into a sample holder 101. Sample holder 101 may include a transparent window 102 into which the sample is dispersed for sensing as is described in more detail below. For example, window 102 may be formed from two closely-spaced transparent plates, between which the sample is dispersed. A vent 105 may be provided to permit air to escape from between the plates as the sample enters. The sample and its included cells disperse into window 102 from one edge, in primary loading direction 106. Sample holder 101 may then be inserted into cell counting system 100, via slot 103. Example cell counting system 100 preferably includes components for sensing an image of transparent window 102, and may also include elements for analyzing the image to determine the number of cells visible in the image. Test results may be presented to a user on a display 104.

Figure 2:
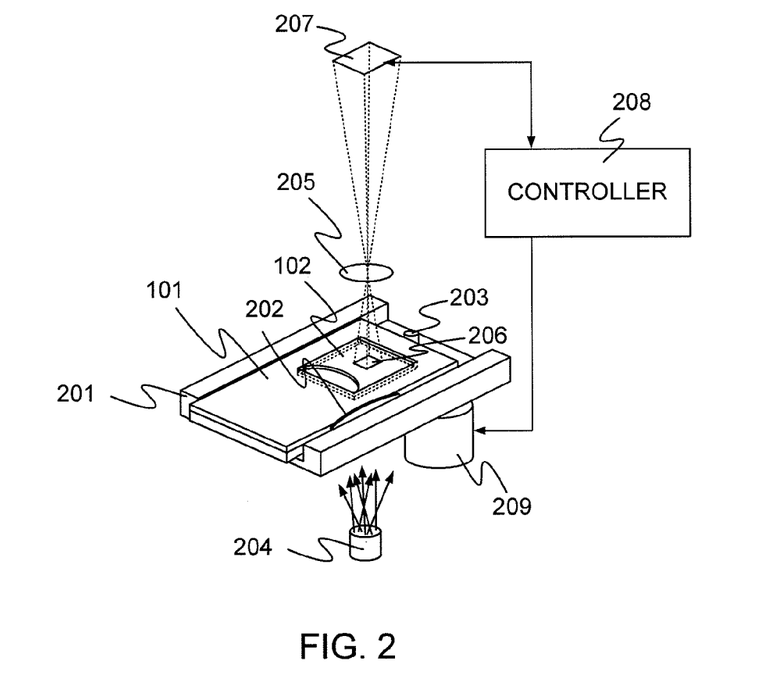
FIG. 2 schematically illustrates a set of components that may be present in the cell counting system of FIG. 1.

FIG. 2 schematically illustrates a set of components that may be present in cell counting system 100. In the embodiment of FIG. 2, sample holder 101 is disposed within a tray 201 that guides sample holder as it is inserted into cell counting system 100. A spring 202 may be used to bias sample holder 101 toward one side of tray 201, for consistent registration. A travel stop 203 limits the insertion of sample holder 101, and registers sample holder 101 at the correct insertion depth. It will be recognized that the features for holding and registering sample holder 101 shown in FIG. 2 are examples only, and that any suitable system for holding and registering sample holder 101 may be used.

A light source 204 illuminates at least a portion of window 102. For example, tray 201 may include a cutout portion (not visible in FIG. 2) that enables light from light source 204 to reach window 102. Light source 204 may be any suitable kind of light source, for example a light emitting diode (LED), an incandescent light source, a fluorescent light source, or another kind of light source. Light source 204 may be monochromatic, may emanate light in a narrow spectrum of wavelengths, or may emanate light in a broad spectrum.

A lens 205 projects an image of a viewing area 206 onto an array light sensor 207. Viewing area 206 includes only a portion of window 102. For example, window 102 may be about 6 by 9 millimeters, while viewing area may be cover an area about 2 by 2 millimeters, although other dimensions may be used.

Array light sensor 207 may be a charge coupled device (CCD) sensor, a complementary metal oxide semiconductor (CMOS) sensor, or another kind of electronic image sensor. Such a sensor includes an array of light-sensitive sites called pixels. Each sensor pixel accumulates electric charge at a rate proportional to the intensity of light falling on the pixel. To read a digital image of viewing area 206, the sensor pixels may be reset, and the sensor exposed to light for a fixed time period. The amount of charge at each pixel is converted to a voltage, and the voltages are read and converted to numerical values. The digital image is an array of the numerical values representing the light intensities falling on the respective pixels. In some embodiments, color information may be gathered as well. In some embodiments, array light sensor 207 may include about 4 million pixels.

A controller 208 interacts with array light sensor 207 to gather the digital image. For example, depending on the sensor type, the controller may provide timing signals to array light sensor 207, may provide configuration information, or other control signals. Controller 208 also receives information indicating the light readings taken at the pixels. Depending on the sensor type and system architecture, the information may be in the form of analog voltages to be converted to digital values by controller 208, or may already have been converted to digital values at sensor 207. Many different system architectures are possible for gathering digital images of viewing area 206.

A motor 209 or other actuator may also be present, as will be described in more detail below. A focusing mechanism may be provided. For example, lens 205 or sensor 207 may be moved manually or automatically along the optical axis to achieve best focus.

Figure 3:
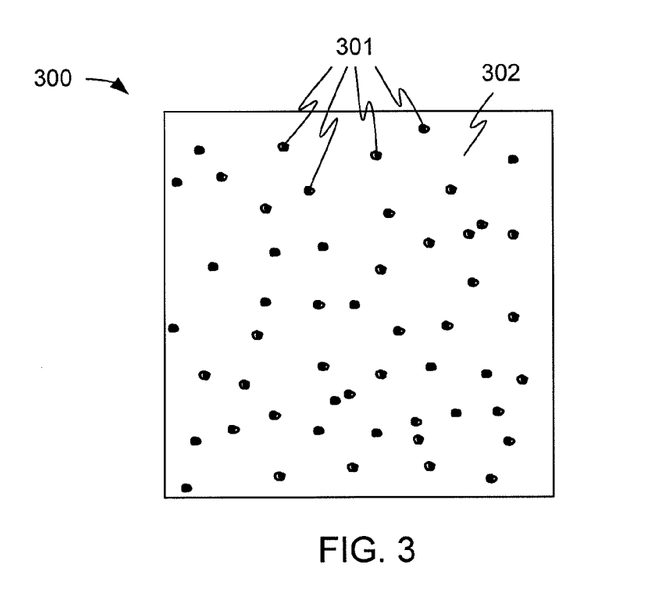
FIG. 3 illustrates an example digital image as may be taken by the cell counting system of FIG. 1.

FIG. 3 illustrates an example digital image 300 as may be taken by cell counting system 100 of viewing area 206, when a sample is present. About 52 cells 301 (only a few of which are labeled) are visible in image 300. In the array of numerical values that make up the digital image, the cells are present as associated groups of values that differ from values associated with the background 302 of the image. In some embodiments, the system utilizes a computerized method according to known techniques to locate and group the values that indicate the presence of cells, and counts the number of cells present in the image. In some embodiments, the system may also characterize the cells, for example counting live and dead cells separately, or distinguishing types of cells. In other embodiments, the images taken by the cell counting system may be simply displayed and the image analysis and cell counting may be performed manually. In still other embodiments, the images taken by the cell counting system may be transferred to another system, for example a computer system, for analysis and cell counting. In other embodiments, images taken by the cell counting system may simply be viewed, without actually counting the cells, and it is intended that the appended claims encompass this use of the system.

Figure 4:
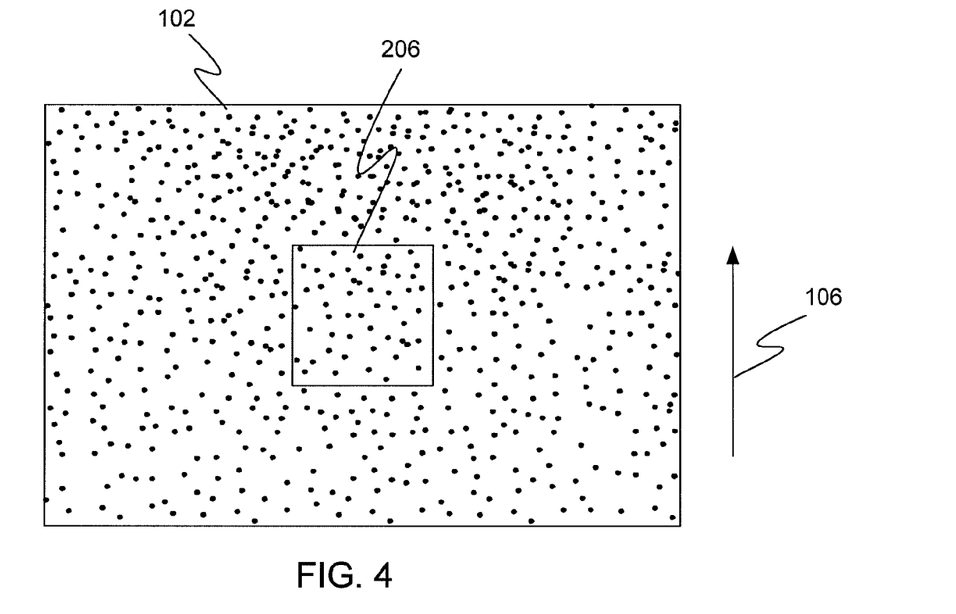
FIG. 4 illustrates a relationship of a viewing area imaged by the system of FIG. 1 to a window of a sample holder.

FIG. 4 illustrates the relationship of viewing area 206 to window 102. Because the sample being measured has a relatively high concentration of cells, the number of cells found within viewing area 206 in relation to the area of viewing area 206 is representative of the concentration of the cells in the sample. That is, in this idealized example, the number of cells per unit area as measured in viewing area 206 is substantially the same as the number of cells per unit area as would be measured across all of window 102. Under these conditions, repeated tests of samples from the same source would likely give results with very little variation of the number of cells counted, in comparison to the number of counted cells.

Figure 5:
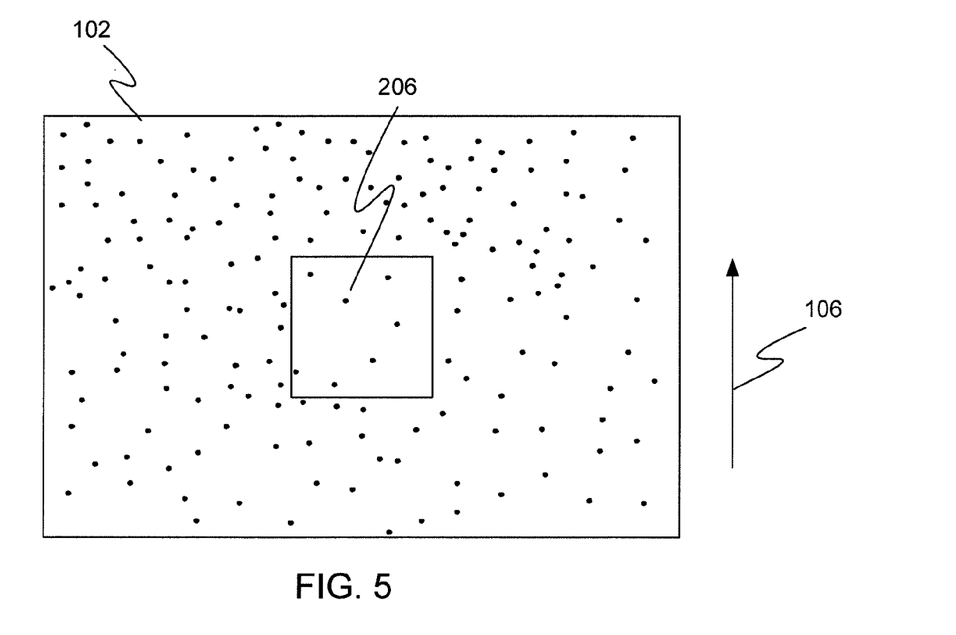
FIG. 5 illustrates another example image of a sample having a lower concentration of cells than are shown in the digital image of FIG. 3.

FIG. 5 illustrates another example test of a sample having a much lower concentration of cells. In fact, only seven cells appear within viewing area 206. As can be seen, other areas of window 102 have cells clustered more closely together, so the number of cells counted within viewing area 206 may not be an accurate representation of the concentration of the sample. If this sample were to be tested again, it would be statistically likely that the cells in the second test would, by chance, disperse in a different way, and the number counted within viewing area 206 would be significantly different.

One measure of the variability of test results is the coefficient of variation (COV), which may be defined as $$COV = \sigma/\mu * 100$$

where $\sigma$ is the standard deviation of the results of a number of tests on samples of a particular material, and $\mu$ is the mean of the test results. As is apparent, COV indicates the variability of test results in relation to the magnitude of the mean result. The multiplier of 100 is optional, and when used, expresses the results as a percentage. Materials with low cell concentrations may be especially susceptible to large COVs, in part because the denominator $\mu$ in the expression for COV is small for materials with low cell concentrations. In general, it is desirable to reduce the variability of test results, whether measured by COV or another characteristic, so that the test results can be reported with confidence and repeated tests can be avoided.

Figure 6:
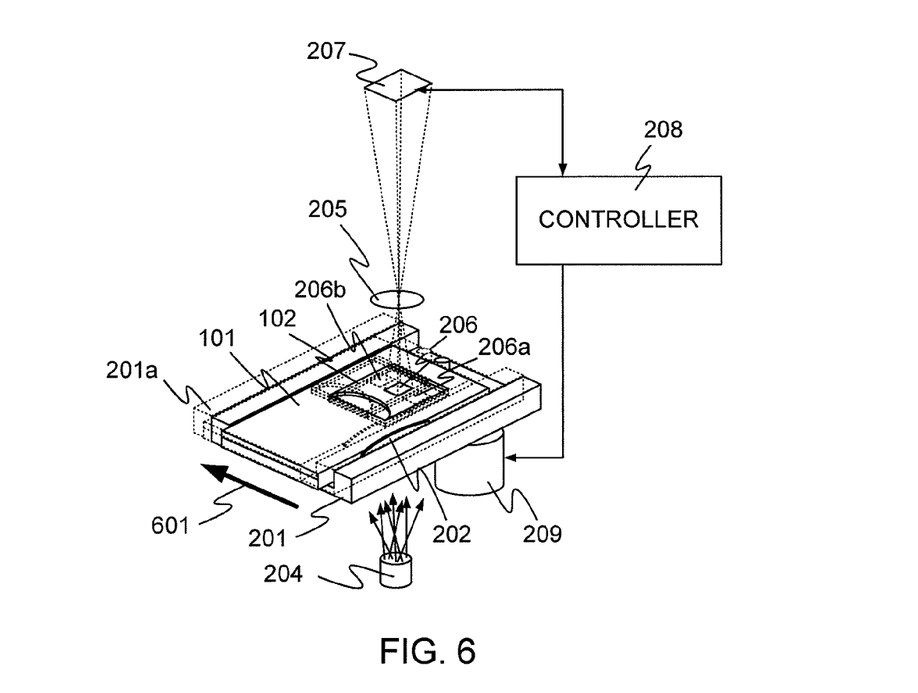
FIG. 6 illustrates the operation of the cell counting system of FIG. 1, according to an embodiment of the invention.

FIG. 6 illustrates the operation of cell counting system 100 according to an embodiment of the invention. In the example shown in FIG. 6, tray 201 is movable with respect to lens 205, so that the relative positions of sample holder 101 and the sensing system are variable. For example, tray 201 may be translated in direction 601 to position 201a, shown in broken lines. Sample holder 101 is carried with tray 201, such that the viewing area imaged by image sensor 207 encompasses area 206a of window 102. Tray 201 may also be movable in the opposite direction to another position (not shown) in which the viewing area imaged by sensor 207 encompasses area 206b of window 102. The movement of tray 201 may be accomplished by a motion system, which may include a motor such as motor 209 or another kind of actuator. Thus, the relative positions of the sensing system and sample holder 101 can be changed to a plurality of configurations, where the viewing area imaged by sensor 207 encompasses a different viewable portion of the sample holder in each configuration. In this example, three different configurations are available, although it will be recognized that two configurations may be utilized, or more than three configurations may be available.

Figure 7:
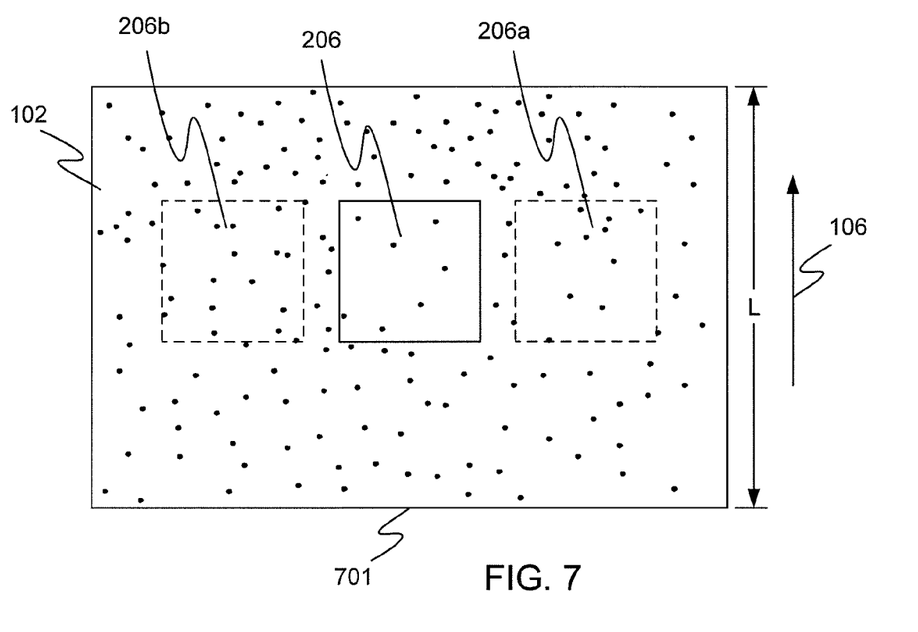
FIG. 7 illustrates an effect of the motion depicted in FIG. 6.

FIG. 7 illustrates the effect of the motion of tray 201, as seen at window 102. The three areas 206, 206a, and 206b imaged by sensor 207 in the three configurations are shown superimposed on window 102.

To count the cells in the sample being measured, controller 208 directs the sensing system to capture a digital image when the sample holder and sensing system are in each of the plurality of configurations, and the digital images are analyzed to count the cells present in the viewing area in all of the digital images. As can be seen in the example of FIG. 7, this results in a larger effective measurement area, and a larger number of cells counted for the sample. The larger effective measurement area reduces the likelihood that the cells in subsequent samples would disperse in such a way that the total number of counted cells would differ significantly in relation to the average number of counted cells. If COV is used as a measure of variability, the COV is reduced, as compared with a test using only a single image.

While the three areas 206, 206a, and 206b imaged by the system of FIG. 6 do not overlap or touch, this is not a requirement. Touching or overlapping viewing areas could be used. The system may perform a correlation operation to identify cells that appear in any overlap regions, to avoid double counting of cells.

In the example system of FIG. 6, tray 201 is moved in translation to expose different portions of window 102 to sensor 207. In other embodiments, other kinds of motions may be used, for example motions resulting in rotation of sample holder 101, combined translation and rotation of sample holder 101, motion of the sensing system while sample holder 101 is held stationary, or motions of both sample holder 101 and the sensing system, so long as the relative positions of the sample holder and the sensing system move to a plurality of configurations such that the viewing area imaged by sensor 207 encompasses a different viewable portion of the sample holder in each configuration.

As is visible in FIGS. 4, 5, and 7, the cells may disperse into window 102 with a gradient in cell density. Typically, cell distribution may be less dense in the portion of window 102 near the loading point, and more dense in portions of window removed from the loading point. That is, cell distribution may not be uniform as the window is traversed in the loading direction 106. The transverse motion of sample holder 101 in gathering the multiple digital images may ensure that the portions of window 102 imaged by the system come from portions of window 102 with generally consistent cell distribution, and may further contribute to repeatability and accuracy of the test results, as compared with a system that moves the sample holder generally parallel to loading direction 106. Even so, in some embodiments, motion generally parallel to loading direction 106 of the sample into sample holder 101. In other embodiments, motion parallel to the loading direction of sample holder 101 into cell counting system 100 may be used. The loading direction 106 of the sample into the sample holder may be the same or different than the loading direction of the sample holder into the cell counting system. The areas imaged are also preferably selected so that cell counts produced by the system are consistent with those produced by other methods. In one example embodiment having a window with a length "L" of about 9.0 millimeters, the areas imaged by the system are centered about 6.3 millimeters from the window edge nearest loading point 701, as shown in FIG. 7.

Figure 8:
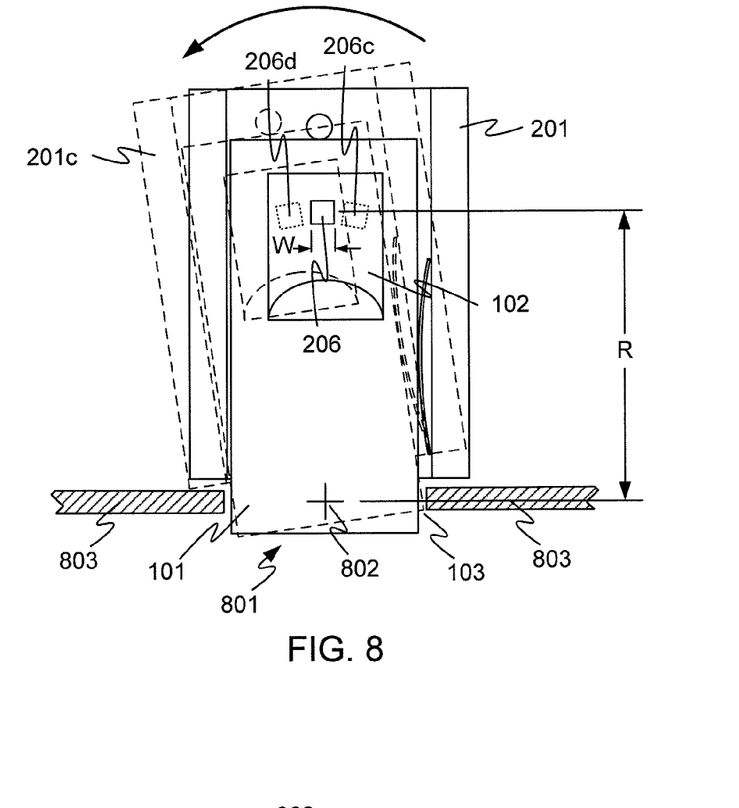
FIG. 8 illustrates a top view of another example motion of a sample holder.

FIG. 8 illustrates a top view of another example motion of sample holder 101. As is shown in FIG. 1, sample holder 101 may be inserted into a slot or other receptacle such as slot 103 in cell counting system 100. Thus, the visible end 801 of sample holder 101 may be constrained from significant lateral translation by walls 803 of the enclosure of cell counting system 100. Motion of tray 201 to expose multiple areas of window 102 to sensor 207 may be provided by a rotational or rocking motion of tray 201 and sample holder 101. In the example illustrated in FIG. 8, tray 201 rotates about an axis 802 at slot 103. While axis 802 is positioned near the center of slot 103, other axes may be chosen, for example an axis at one edge of slot 103. In other embodiments, a rotational axis maybe used that is not near slot 103.

In the example of FIG. 8, when tray 201 is rotated to position 201c, shown in broken lines, then the viewing area imaged by image sensor 207 encompasses area 206c of window 102. Tray 201 may also be rotated in the opposite direction to expose area 206d of window 102 to sensor 207. Because axis 802 is removed from window 102, the rotation of sample holder 101 results in a generally transverse change in the position of viewing area 206 with respect to window 102. Thus, areas 206, 206c, and 206d may all encompass portions of window 102 having similar cell distribution. Preferably, to achieve generally transverse apparent motion of viewing area 206 within window 102, the axis of rotation of sample holder 101 is removed from viewing area 206 by a distance "R" that is at least 5 times the width "W" of viewing area 206, and more preferably by at least 8 times the width of viewing area 206. In some embodiments, the rotational axis may be removed by 10, 15, or more times the width of viewing area 206.

Figure 9:
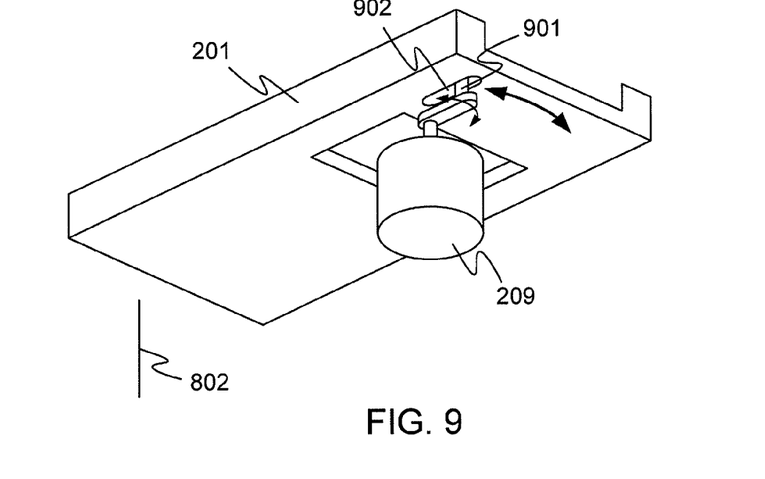
FIG. 9 illustrates a lower oblique view of one example motion system for providing the rocking motion illustrated in FIG. 8.

FIG. 9 illustrates a lower oblique view of one example motion system for providing the rocking motion illustrated in FIG. 8. In the system of FIG. 9, rotation of motor 209 drives an eccentric pin 901, which in turn engages slot 902 in tray 201. The motion of eccentric pin 901 drives slot 902, and consequently tray 201 and sample holder 101, to expose different areas of window 102 to sensor 207.

Motor 109 may be any suitable kind of motor, for example a stepper motor, a DC servo motor, or another kind of motor. Limit switches or other means may be provided for limiting the rotational travel of motor 109. In other embodiments, other kinds of actuators and motion systems may be utilized, for example a linear motor, a solenoid, a pneumatic or hydraulic actuator or another kind of actuator may drive tray 102 through gears, belts, pulleys, direct drive, friction drive, or another suitable mechanism.

Figure 10:
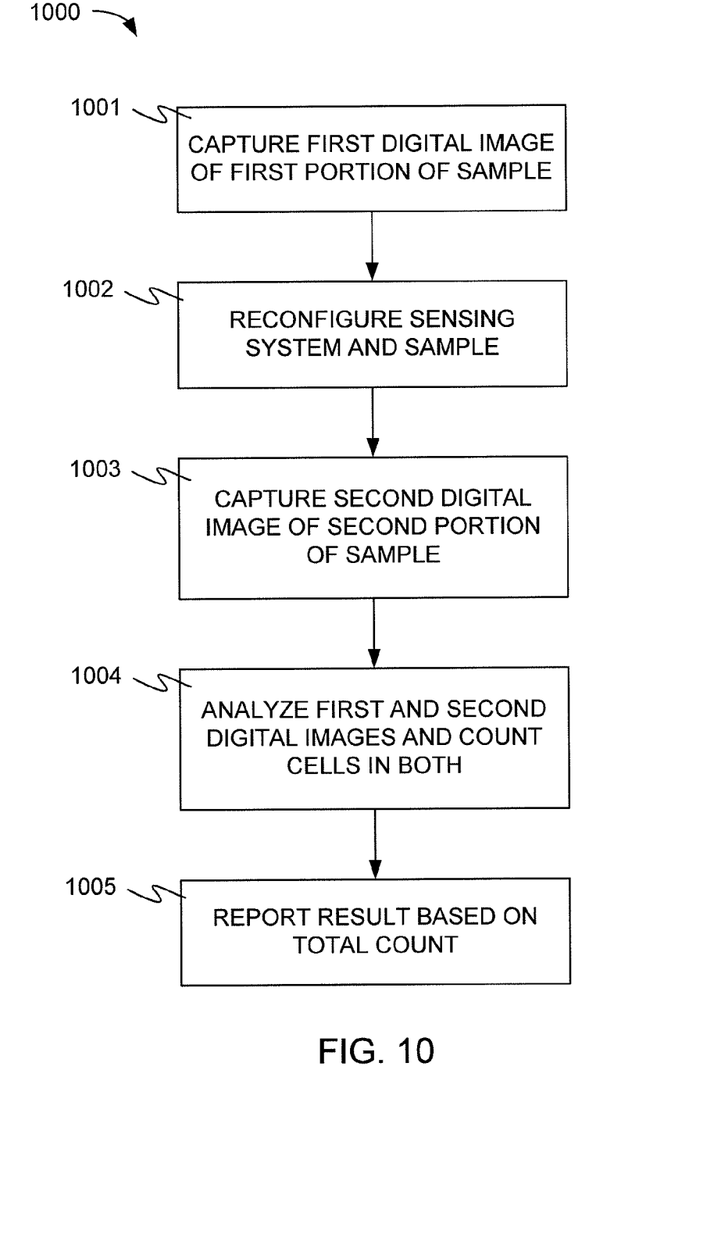
FIG. 10 illustrates a flow chart of a method for counting cells, in accordance with an embodiment of the invention.

FIG. 10 illustrates a flow chart of a method 1000 for counting cells, in accordance with an embodiment of the invention. In step 1001, a digital image is captured of a first viewable portion of a sample containing cells to be counted. In step 1002, the relationship of the a sensing system and the sample is reconfigured, such that the sensing system images a second viewable portion of the sample. In step 1003, a second digital image is captured of the second viewable portion. In step 1004, the first and second digital images are analyzed, and the cells detected in both of the digital images are counted. In step 1005, a test result is reported that is based on the count of the cells in both the first and second images. For example, if 23 cells were detected in the first digital image and 29 cells were detected in the second digital image, a count of 52 total cells may be reported. In other embodiments, other kinds of values based on the cell count may be reported. For example, the cell count may be converted to a concentration of cells, and the cell concentration may be reported.

It will be recognized that more than two digital images may be captured, each digital image being of a different viewable portion of the sample. For example, three, four, or more viewable areas and respective digital images may be utilized, and test results reported based on the combined count of cells appearing in all of the digital images. It will also be recognized that the steps may be performed in any workable order. For example, both digital images may be captured before either is analyzed.

Figure 11:
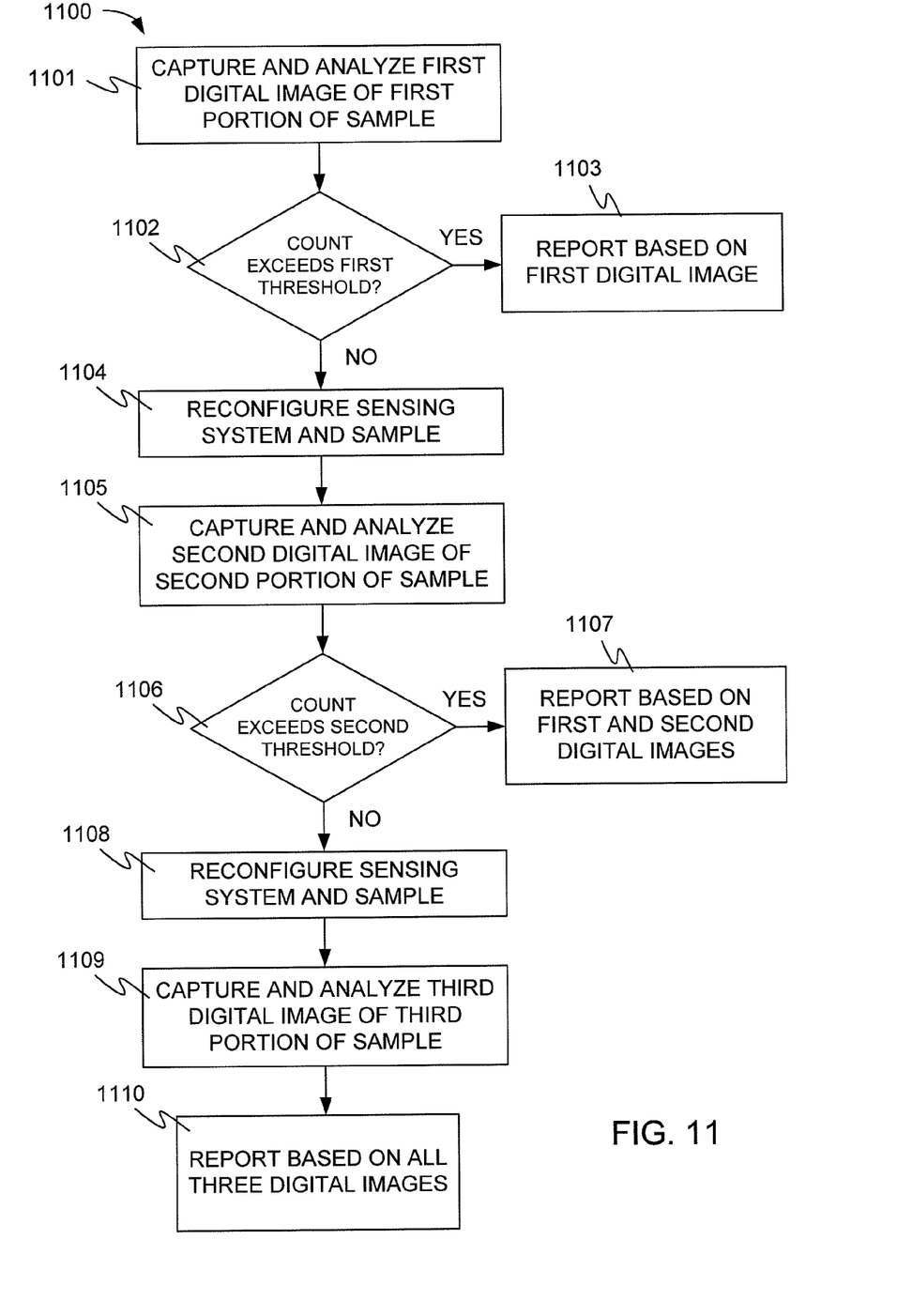
FIG. 11 illustrates a flow chart of a method for counting cells, in accordance with other embodiments.

FIG. 11 illustrates a flow chart of a method 1100 for counting cells, in accordance with other embodiments. In some tests, for example in testing a sample having a high concentration of cells, counting the cells in a single digital image may be sufficient to give a concentration estimate that is repeatable and reliable. In such a case, further testing does not provide a significant advantage in accuracy or repeatability, and incurs additional testing time in reconfiguring the sensing system and sample, capturing an additional image, and analyzing the additional image. Method 1100 recognizes that some tests may require analysis of only a single digital image to achieve satisfactory results, while other tests may require analysis of two or more digital images.

In step 1101, a first digital image is captured of a first viewable portion of a sample containing cells to be counted, and the digital image is analyzed to count the number of cells detected in the first digital image. This count represents an estimate of the concentration of cells in the sample. In step 1102, the count is compared with a first threshold chosen to distinguish tests where analysis of a single digital image is sufficient to obtain a satisfactory concentration estimate and tests where multiple images are needed. If the count obtained from analysis of the first digital image exceeds the first threshold, a test result based on the cell count in the first digital image is reported at step 1103.

When the count of cells in the first digital image does not exceed the first threshold, the sensing system and sample are reconfigured such that the sensing system images a second viewable portion of the sample. In step 1105, a second digital image is captured of the second viewable portion of the sample, and the second digital image is analyzed to determine a cell count. At step 1106, the combined count of cells detected in the first and second images is compared with a second threshold. If the combined count exceeds the threshold, a test result is reported in step 1107, based on the combined count of cells appearing in the first and second digital images. If the combined count does not exceed the second threshold, then the system is again reconfigured in step 1108, so that the sensing system images a third viewable portion of the sample. At step 1109, a third digital image is captured of the third viewable area of the sample, and the third digital image is analyzed. In step 1110, a test result is reported based on the combined cell count of all three images.

Other variations are possible. For example, a plurality of digital images could be obtained of different viewing areas of the sample before any image analysis is performed. A first one of the plurality of images may then be analyzed, and if the analysis indicates that enough cells were detected that additional testing is unnecessary, the result may be reported, analysis of any other digital images may be foregone, and any unused digital images discarded. If analysis of the first digital image indicates that the cell concentration was too low for a satisfactory result, then a second one of the plurality of digital images may be analyzed. If the analysis of the second digital image indicates that the first and second digital images provide satisfactory results, the results is reported, and analysis of any further images is foregone.

Figure 12:
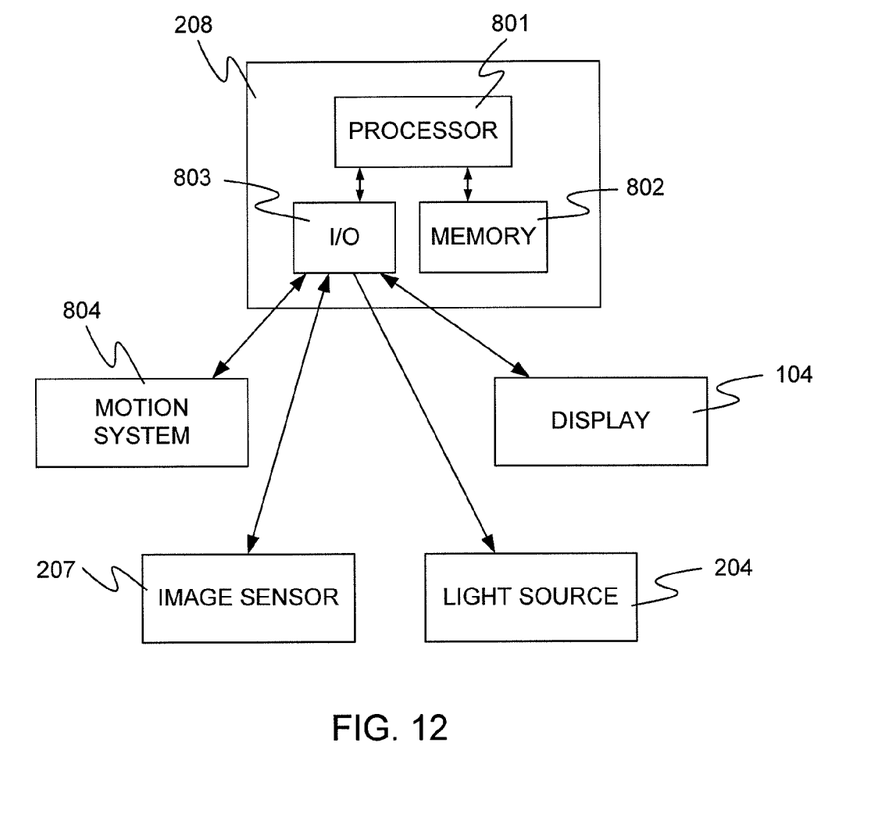
FIG. 12 illustrates one example architecture of a self-contained cell counting system.

Systems according to embodiments of the invention may have a variety of electronic architectures. FIG. 12 illustrates one example architecture of a self-contained cell counting system such as system 100 illustrated in FIG. 1. In the embodiment of FIG. 12, controller 208 includes a processor 801. Processor 801 may be any suitable kind of processor, such as a general purpose microprocessor or microcontroller. Processor 801 accesses memory 802, which may comprise volatile memory and nonvolatile memory. For example, memory 802 may include nonvolatile memory, such as flash memory or programmable read-only memory, holding microprocessor instructions that, when executed by processor 801, cause controller to carry out its programmed functions. Input/output module 803 may include one or more interfaces to other parts of the system, including motion system 804 (which may include motor 209 or another kind of actuator), image sensor 207, light source 204, and display 104. In this example embodiment, memory 802 may hold instructions that cause processor 801 to direct the configuration of the system and the gathering of digital images, and may also include instructions for the analysis of the digital images to identify and count cells, and for reporting results.

Figure 13:
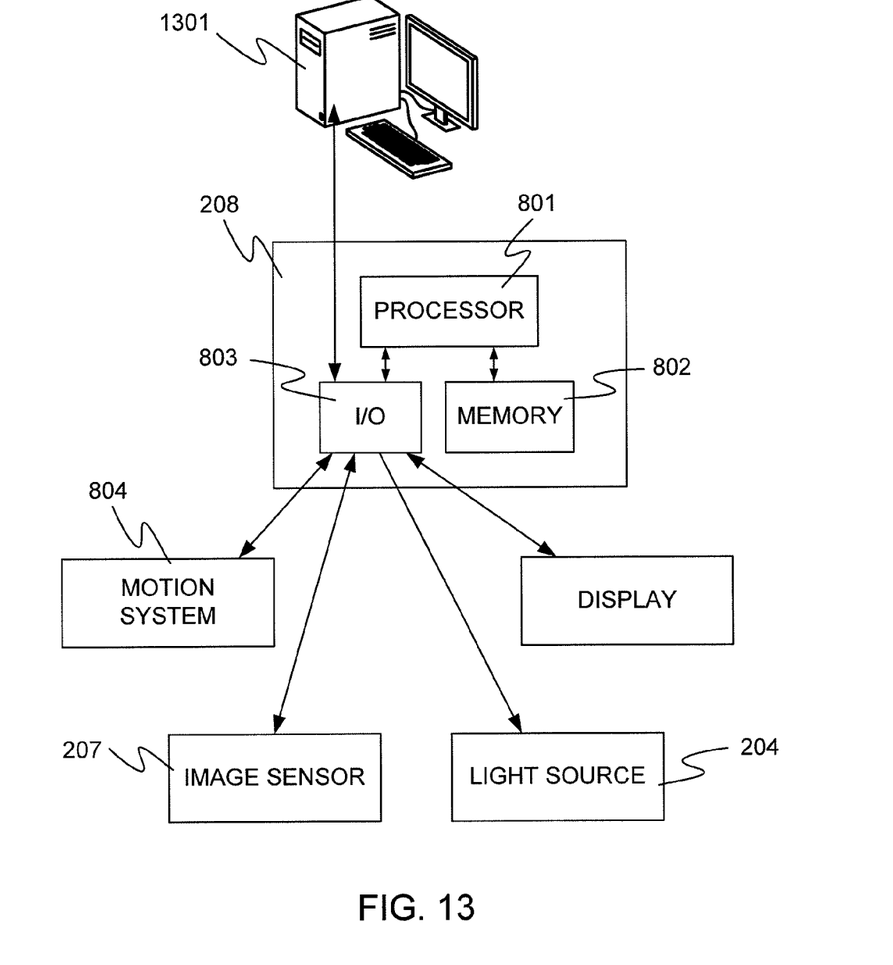
FIG. 13 illustrates another example architecture of a cell counting system, including an external computer system.

FIG. 13 illustrates another example architecture of a cell counting system that includes an external computer system 1301. For example, controller 208 may transmit digital images captured by image sensor 207 to computer system 1301 for analysis and reporting of results. It will be recognized that tasks performed by cell counting systems according to embodiments of the invention may be allocated in any number of ways between hardware, software, and firmware, and between different internal processors and external computer systems. It is intended that the claims not be limited to any particular electronic architecture.

Figure 14:
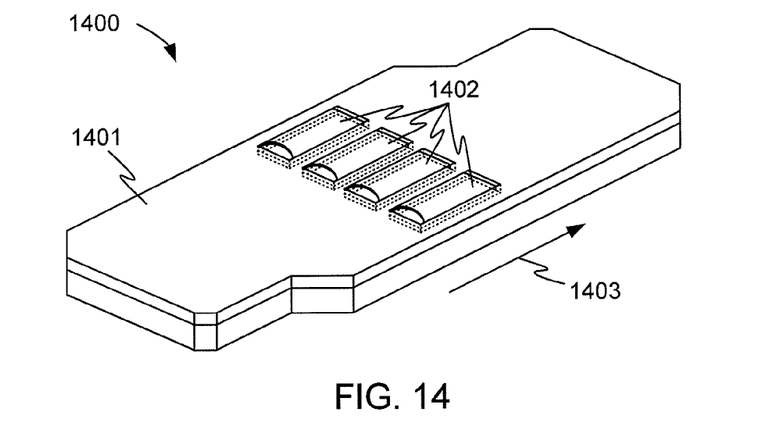
FIG. 14 illustrates a sample holder in accordance with embodiments of the invention.

FIG. 14 illustrates a sample holder 1400 that may be conveniently used in conjunction with cell counting systems and methods according to embodiments of the invention. Sample holder 1400 comprises a body 1401 that is configured for insertion into a cell counting system, for example a cell counting system as described above. Sample holder 1400 also includes multiple windows 1402 into which samples may be placed. Example sample holder 1400 includes four windows 1402, but more or fewer may be used. Preferably, the locations of windows 1402 correspond to the locations of viewing areas such as viewing area 206, which a cell counting system according to embodiments may present to a sensor such as sensor 207 for digital imaging. In one example use, an amount of a sample may be placed into one or more of windows 1402. Sample holder 1400 may then be placed into a cell counting system according to an embodiment of the invention, and more than one of windows 1402 may be imaged. The samples in the multiple windows being utilized may be of the same material or different materials, in any combination.

Figure 15:
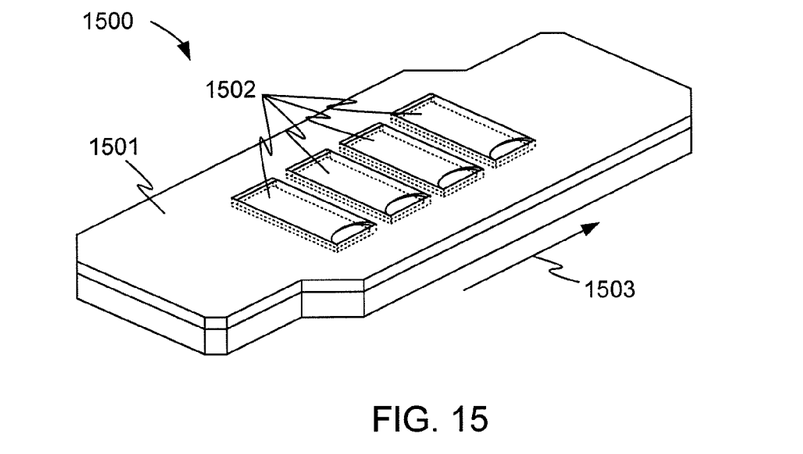
FIG. 15 illustrates a sample holder in accordance with other embodiments.

In sample holder 1400, windows 1402 are arranged transversely to a primary loading direction 1403 of sample holder 1400 into a cell counting system. FIG. 15 shows another example sample holder 1500, comprising a body 1501 and multiple windows 1502 arranged parallel to a primary loading direction 1503 of sample holder 1501 into a cell counting system.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. The invention has now been described in detail for the purposes of clarity and understanding. However, those skilled in the art will appreciate that certain changes and modifications may be practiced within the scope of the appended claims.

What is claimed is:

1. A system, comprising:
   a sensing system that produces a digital image of a viewing area of a sample holder, the sample holder holding a set of cells;
   a motion system that changes the relative positions of the sample holder and the sensing system to a plurality of configurations, such that the viewing area encompasses a different viewable portion of the sample holder in each configuration, wherein the encompassed viewable portions are arranged transversely with respect to a primary loading direction of the sample into the sample holder;
   an enclosure housing at least some of the system and defining a slot into which the sample holder is inserted, and wherein the motion system rotates the sample holder while one end of the sample holder remains between sides of the slot;
   a controller including a processor and a memory holding instructions that when executed by the processor direct the sensing system to capture a digital image when the sample holder and sensing system are in each of the plurality of configurations;
   a computerized analyzer that analyzes the digital images and counts the cells detected in all of the digital images; and
   a display on which cell counting results are displayed.

2. The system of claim 1, wherein the controller performs the function of the computerized analyzer.

3. The system of claim 1, further comprising a light source that illuminates the viewing area.

4. The system of claim 1, wherein the viewable portions of the sample holder encompassed by the viewing area in the plurality of configurations do not overlap.

5. The system of claim 1, wherein the motion system further comprises a translation mechanism that moves the sample holder in translation.

6. The system of claim 1, the motion system rotates the sample holder in a rocking motion while one end of the sample holder remains between sides of the slot.

7. The system of claim 6, wherein the rotation system rotates the sample holder about a point at the slot.

8. The system of claim 1, wherein the motion system comprises a motor that moves the sample holder under control of the controller.

9. The system of claim 1, wherein the plurality of configurations includes at least three configurations.

10. The system of claim 1, further comprising the sample holder, wherein the viewable portions of the sample holder are located in a single window of the sample holder.

11. A system, comprising:
a sample holder;
a sensing system that produces a digital image of a viewing area of a the sample holder, the sample holder holding a set of cells;
a motion system that changes the relative positions of the sample holder and the sensing system to a plurality of configurations, such that the viewing area encompasses a different viewable portion of the sample holder in each configuration, wherein the encompassed viewable portions are arranged transversely with respect to a primary loading direction of the sample into the sample holder; wherein the viewable portions of the sample holder are located in different windows of the sample holder;
a controller including a processor and a memory holding instructions that when executed by the processor direct the sensing system to capture a digital image when the sample holder and sensing system are in each of the plurality of configurations;
a computerized analyzer that analyzes the digital images and counts the cells detected in all of the digital images; and
a display on which cell counting results are displayed.

12. The system of claim 11, wherein the at least two windows hold different sample materials.

13. A method, comprising:
capturing, using a sensing system, a first digital image of a first viewable portion of a sample containing cells;
reconfiguring the sensing system and sample such that the sensing system images a second viewable portion of the sample, wherein the first and second viewable portions are arranged transversely with respect to a primary loading direction of the sample into a sample holder holding the sample wherein reconfiguring the sensing system and sample comprises rotating the sample holder while one end of the sample holder remains between sides of a slot in an enclosure that houses at least some of the sensing system;
capturing a second digital image of the second viewable portion;
analyzing, using a computerized analyzer, the first and second digital images and counting the cells detected in the digital images; and
reporting a test result based on the count of the cells in both the first and second images.

14. The method of claim 13, further comprising:
reconfiguring the sensing system and sample such that the sensing system images a third viewable portion of the sample;
capturing a third digital image of the viewing area; and
analyzing the third digital image and counting the cells detected in the third digital image;
wherein reporting a test result based on the count of the cells in both the first and second images comprises reporting a test result based on the count of cells in all three of the digital images.

15. The method of claim 13, wherein the first viewable portion and the second viewable portion do not overlap.

16. The method of claim 13, wherein reconfiguring the sensing system and sample comprises moving the sample.

17. The method of claim 13, wherein reconfiguring the sensing system and sample comprises moving at least a portion of the sensing system.

18. The method of claim 13, wherein reconfiguring the sensing system and sample comprises moving both the sample and at least a portion of the sensing system.

19. The method of claim 13, wherein the first and second viewable portions are located in a single window of the sample holder.

20. The method of claim 13, wherein the first and second viewable portions are located in different windows of the sample holder.

21. A method of counting cells, the method comprising:
capturing, using a sensing system, a first digital image of a first viewable portion of a sample containing cells;
analyzing, using a computerized analyzer, the first digital image to obtain a count of the cells present in the first digital image;
comparing the count with a threshold count;
when the count is below the threshold count, reconfiguring the sensing system and sample such that the sensing system images a second viewable portion of the sample;
capturing a second digital image of the second viewable portion; and analyzing the second digital image and reporting a test result based on the count of the cells present in the first and second digital images; and
when the count is above the threshold count, reporting a test result based on a count of the cells present in the first digital image without capturing a second digital image;
wherein the first and second viewable portions are arranged transversely with respect to a primary loading direction of the sample into the sample holder;
wherein the count is a first count and the threshold count is a first threshold count, the method further comprising, when the first count is below the first threshold count;
analyzing the first and second digital images to compute a second count of the cells present in the first and second digital images;
comparing the second count with a second threshold count;
when the second count is below the second threshold count, reconfiguring the sensing system and sample such that the sensing system images a third viewable portion of the sample; capturing a third digital image of the third viewable portion; and analyzing the third digital image and reporting a test result based on a count of the cells present in the first, second, and third digital images; and
when the second count is above the second threshold count, reporting a test result base on a count of the cells present in the first and second digital images without capturing a third digital image.

22. The method of claim 21, wherein the first and second threshold counts are the same.

23. A method of counting cells, the method comprising:
capturing, using a sensing system, a plurality of digital images of different viewable portions of a sample containing cells, wherein the sensing system is reconfigured between captures of two of the viewable portions by rotating a sample holder holding the sample while one end of the sample holder remains between sides of a slot in an enclosure that houses at least some of the sensing system;

analyzing, using a computerized analyzer, a first one of the plurality of digital images to obtain a first count of the cells present in the first digital image;

comparing the count with a threshold count;

when the count is below the threshold count, analyzing at least one additional image from the plurality of digital images and reporting a test result based on the count of the cells present in the analyzed digital images; and when the count is above the threshold count, reporting a test result based on a count of the cells present in the first digital image without analyzing any further digital images.

24. The system of claim 1, further comprising the sample holder, the sample holder including:

a body configured for insertion into a cell counting system;

a plurality of windows in the body for receiving samples of one or more materials containing cells to be counted, the plurality of windows being arranged transversely or parallel with respect to a primary loading direction of the sample holder into the cell counting system.

25. The system of claim 24, wherein the windows are spaced apart from each other by a distance corresponding to the spacing of multiple viewing areas of the cell counting system.

26. A method, comprising:

capturing, using a sensing system, a first digital image of a first viewable portion of a sample containing cells;

reconfiguring the sensing system and sample such that the sensing system images a second viewable portion of the sample, wherein the first and second viewable portions are arranged transversely with respect to a primary loading direction of the sample into a sample holder holding the sample;

capturing a second digital image of the second viewable portion;

analyzing, using a computerized analyzer, the first and second digital images and counting the cells detected in the digital images;

reporting a test result based on the count of the cells in both the first and second images;

comparing the count of cells in the first and second digital images with a threshold count;

when the count of cells in the first and second digital images is below the threshold count, reconfiguring the sensing system and sample such that the sensing system images a third viewable portion of the sample; capturing a third digital image of the third viewable portion; and analyzing the third digital image and reporting a test result based on a count of the cells present in the first, second, and third digital images; and when the count of cells in the first and second digital images is above the threshold count, reporting the test result base on the count of the cells present in the first and second digital images without capturing a third digital image.

* * * * *